(12) United States Patent
Yanagawa et al.

(10) Patent No.: US 10,369,254 B2
(45) Date of Patent: Aug. 6, 2019

(54) METHOD AND APPARATUS FOR IN VITRO KIDNEY ORGANOGENESIS

(71) Applicants: THE REGENTS OF THE UNIVERSITY OF CALIFORNIA, Oakland, CA (US); U.S. Department of Veterans Affairs, Washington, DC (US)

(72) Inventors: Norimoto Yanagawa, Pacific Palisades, CA (US); Masaki Nishikawa, Van Nuys, CA (US); Morgan Hamon, Northridge, CA (US); Peter Viktor Hauser, Los Angeles, CA (US)

(73) Assignees: THE REGENTS OF THE UNIVERSITY OF CALIFORNIA, Oakland, CA (US); U.S. DEPARTMENT OF VETERANS AFFAIRS, Washington, DC (US)

( * ) Notice: Subject to any disclaimer, the term of this patent is extended or adjusted under 35 U.S.C. 154(b) by 235 days.

(21) Appl. No.: 15/121,551

(22) PCT Filed: Feb. 6, 2015

(86) PCT No.: PCT/US2015/017726
§ 371 (c)(1),
(2) Date: Aug. 25, 2016

(87) PCT Pub. No.: WO2015/130919
PCT Pub. Date: Sep. 3, 2015

(65) Prior Publication Data
US 2016/0361466 A1    Dec. 15, 2016

Related U.S. Application Data

(60) Provisional application No. 61/945,022, filed on Feb. 26, 2014.

(51) Int. Cl.
*A61L 27/36* (2006.01)
*C12N 5/071* (2010.01)
(Continued)

(52) U.S. Cl.
CPC ....... *A61L 27/3604* (2013.01); *A61L 27/3683* (2013.01); *C12M 21/08* (2013.01);
(Continued)

(58) Field of Classification Search
None
See application file for complete search history.

(56) References Cited

U.S. PATENT DOCUMENTS

| 5,912,116 A | 6/1999 | Caldwell |
| 7,074,552 B1 * | 7/2006 | Nigam ............... A61L 27/3604 424/93.1 |

(Continued)

FOREIGN PATENT DOCUMENTS

| WO | 2000077170 | 12/2000 |
| WO | 2003042405 | 5/2003 |
| WO | 2005047529 | 5/2005 |

OTHER PUBLICATIONS

Vinci et al (Biotech. J., 6:554-564 (2011), (Year: 2011).*
(Continued)

*Primary Examiner* — Thomas J. Visone
(74) *Attorney, Agent, or Firm* — Riverside Law LLP

(57) ABSTRACT

The invention provides for a device, system, and methods for using the same with kidney progenitor cells, specifically ureteric bud (UB) cells, metanephric mesenchymal (MM) cells, and the stromal cell (SC) subpopulation of the metanephric mesenchyme, to generate an embryonic kidney organoid that can be implanted into a mammalian subject to create a living, functional kidney.

19 Claims, 17 Drawing Sheets

(51) Int. Cl.
*C12M 3/00* (2006.01)
*C12M 1/12* (2006.01)
*C12M 3/06* (2006.01)
*C12M 1/00* (2006.01)

(52) U.S. Cl.
CPC ............ *C12M 23/16* (2013.01); *C12M 23/58* (2013.01); *C12M 25/14* (2013.01); *C12N 5/0697* (2013.01); *C12N 2502/256* (2013.01)

(56) References Cited

U.S. PATENT DOCUMENTS

| | | | |
|---|---|---|---|
| 7,326,570 B2* | 2/2008 | Nigam | A61K 38/18 424/93.1 |
| 8,148,149 B2* | 4/2012 | Nigam | A61K 38/18 435/325 |
| 8,460,929 B2* | 6/2013 | Nigam | C12N 5/0686 424/93.7 |
| 2002/0012953 A1 | 1/2002 | Jauho et al. | |
| 2003/0166274 A1 | 9/2003 | Hewitt et al. | |
| 2004/0087017 A1 | 5/2004 | Bander et al. | |
| 2005/0074875 A1 | 4/2005 | Nigam et al. | |
| 2008/0070264 A1* | 3/2008 | Sariola | G01N 33/502 435/7.23 |
| 2009/0269800 A1* | 10/2009 | Covey | G01N 35/1095 435/29 |
| 2011/0008892 A1 | 1/2011 | Nigam et al. | |

OTHER PUBLICATIONS

Qiao et al., PNAS, 96:7330-7335 (1999) (Year: 1999).*
Zhang et al, 6'IFPT, Meeting Abstract (2009) (Year: 2009).*
Cullen-McEwen et al., "The where, what and why of the developing renal stroma," Nephron Experimental Nephrology 99.1 (2005): e1-e8.
Das et al. "Stromal—epithelial crosstalk regulates kidney progenitor cell differentiation," Nature cell biology 15.9 (2013): 1035-1044.
Sequeira-Lopez et al. "The earliest metanephric arteriolar progenitors and their role in kidney vascular development," American Journal of Physiology-Regulatory, Integrative and Comparative Physiology 308.2 (2015): R138-R149.
Rogers et al. "Transplantation of rat metanephroi into mice," American Journal of Physiology-Regulatory, Integrative and Comparative Physiology 280.6 (2001): R1865-R1869.
Unbekandt et al., "Dissociation of embryonic kidneys followed by reaggregation allows the formation of renal tissues," Kidney international 77.5 (2010): 407-416.
Ganeva et al. "An improved kidney dissociation and reaggregation culture system results in nephrons arranged organotypically around a single collecting duct system," Organogenesis 7.2 (2011): 83-87.
Hauser et al. "Controlled tubulogenesis from dispersed ureteric bud-derived cells using a micropatterned gel," Journal of tissue engineering and regenerative medicine 10.9 (2016): 762-771.
Takahashi et al. "Induction of pluripotent stem cells from adult human fibroblasts by defined factors," Cell 131.5 (2007): 861-872.
Yu et al. "Induced pluripotent stem cell lines derived from human somatic cells," Science 318.5858 (2007): 1917-1920.
Feng et al. "Molecules that promote or enhance reprogramming of somatic cells to induced pluripotent stem cells," Cell stem cell 4.4 (2009): 301-312.
Scherjon et al., "Amniotic fluid as a novel source of mesenchymal stem cells for therapeutic transplantation," Blood 102.4 (2003): 1548-1549.
Prusa et al., "Oct-4-expressing cells in human amniotic fluid: a new source for stem cell research?," Human reproduction 18.7 (2003): 1489-1493.
Kaviani et al., "The amniotic fluid as a source of cells for fetal tissue engineering," Journal of pediatric surgery 36.11 (2001): 1662-1665.
Prusa et al., "Amniotic fluid cells and human stem cell research: a new connection," Medical Science Monitor 8.11 (2002): RA253-RA257.
Sakurai et al. "An in vitro tubulogenesis system using cell lines derived from the embryonic kidney shows dependence on multiple soluble growth factors," Proceedings of the National Academy of Sciences 94.12 (1997): 6279-6284.
Grobstein, "Morphogenetic interaction between embryonic mouse tissues separated by a membrane filter," Nature 172.4384 (1953): 869-871.
Grobstein, "Trans-filter induction of tubules in mouse metanephrogenic mesenchyme," Experimental cell research 10.2 (1956): 424-440.
Grobstein, "Some transmission characteristics of the tubule-inducing influence on mouse metanephrogenic mesenchyme," Experimental cell research 13.3 (1957): 575-587.
Michos, "Kidney development: from ureteric bud formation to branching morphogenesis," Current opinion in genetics & development 19.5 (2009): 484-490.

* cited by examiner

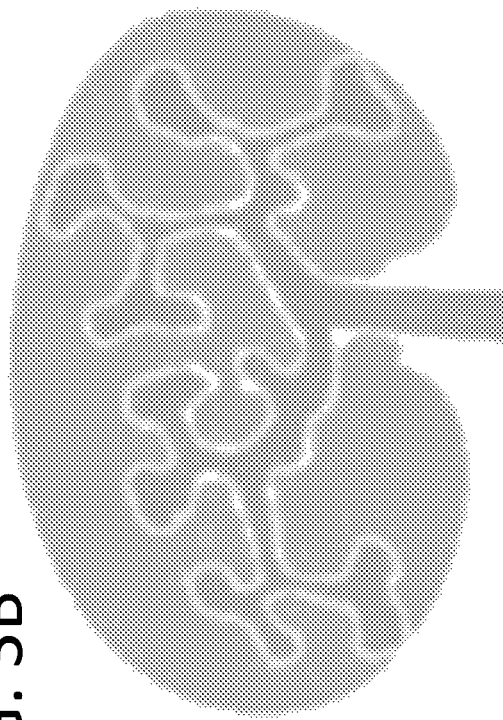
FIG. 3B
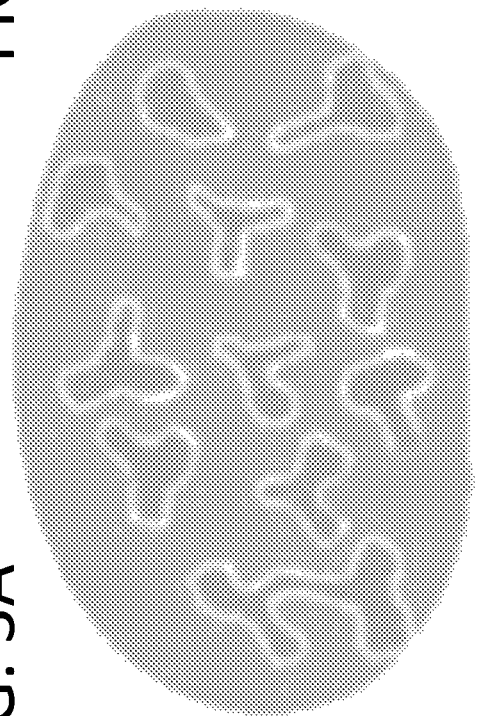
FIG. 3A
FIG. 3A – FIG. 3B

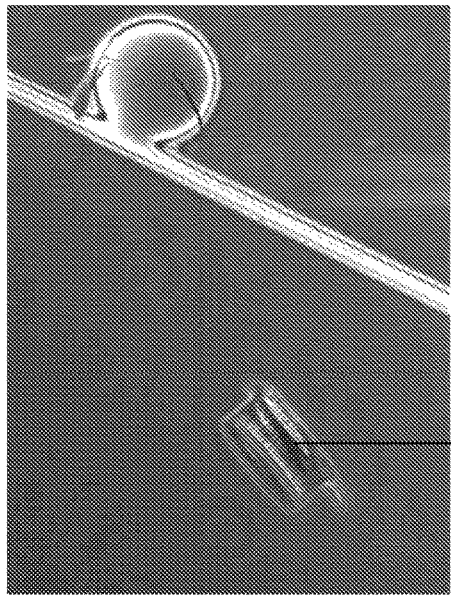
FIG. 10B
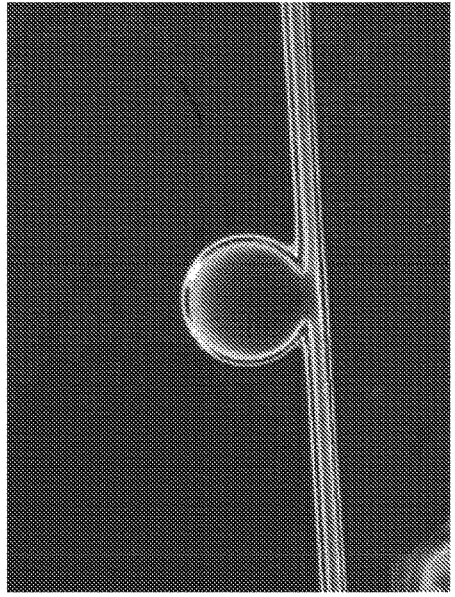
FIG. 10A
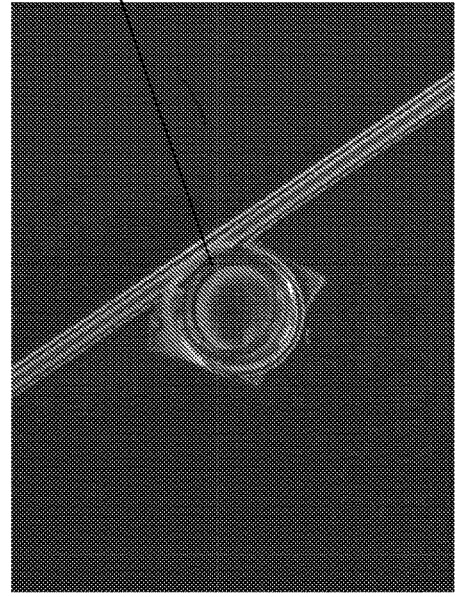
FIG. 10C
FIG. 10A – FIG. 10C

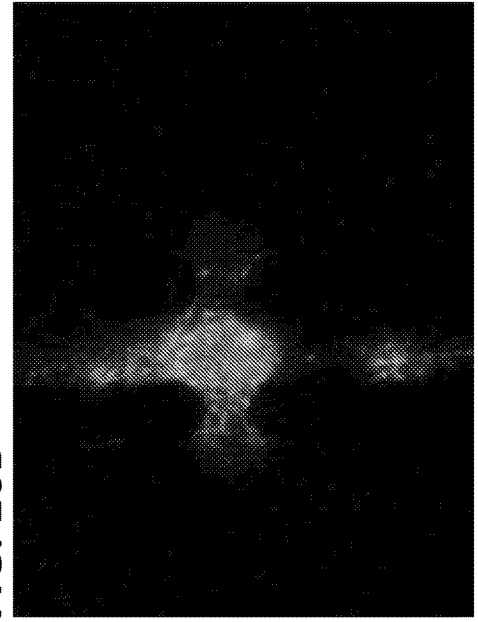
FIG. 16B
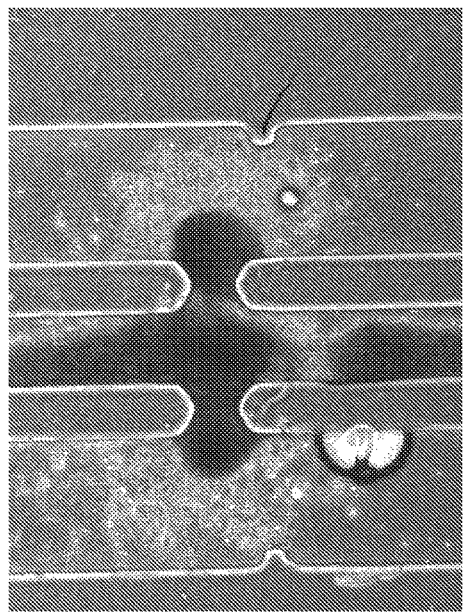
FIG. 16A
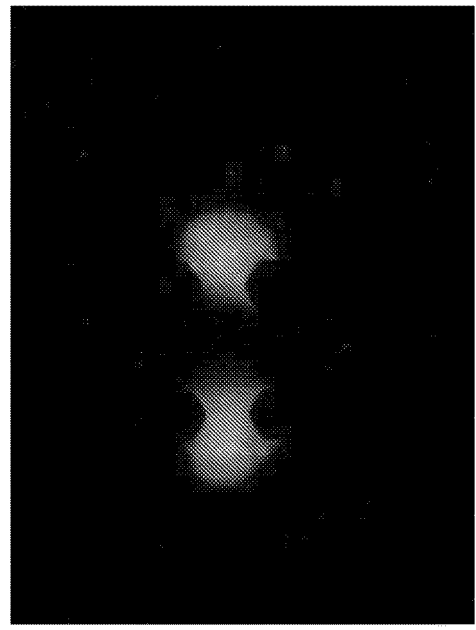
FIG. 16C
FIG. 16A – FIG. 16C

METHOD AND APPARATUS FOR IN VITRO KIDNEY ORGANOGENESIS

CROSS-REFERENCE TO RELATED APPLICATIONS

This application is the U.S. national phase application filed under 35 U.S.C. § 371 claiming benefit to International Patent Application No. PCT/US15/17726, filed Feb. 26, 2015, which is entitled to priority under 35 U.S.C. § 119(e) to U.S. Provisional Patent Application No. 61/945,022, filed Feb. 26, 2014, each of which application is hereby incorporated herein by reference in its entirety.

BACKGROUND OF THE INVENTION

End stage renal disease (ESRD), the permanent loss of kidney function, is an increasing threat to healthcare across all societies worldwide. Currently, the preferred treatment for ESRD is kidney transplantation, but this option is limited by the shortage of donor organs and complications due to rejection and immunosuppression. Dialysis, the second treatment option for ESRD, is cost intensive and associated with morbidity as well as poor quality of life.

Regenerative medicine is working towards developing methods to overcome these limitations through, for example, in vitro kidney organogenesis. The kidney develops from two main cell types, the ureteric bud (UB) cells and the metanephric mesenchymal (MM) cells (FIG. 1). In the embryo, these two cell types are arranged in a specific way. The UB cells take the shape of a tube as an outgrowth of the Wolfian duct (WD), while the MM cells are aggregated in a sphere. Renal development starts when the UB cells are attracted by growth factors released from the MM cells and grow into the MM sphere to form the branched tubular structure of the kidney collecting system. In a reciprocal manner, the UB cells release factors to induce MM cells to differentiate and develop into the remaining structures of the kidney.

A population of cells present in the MM, the stromal cells (SC), also has important functions in the developing kidney. Studies have demonstrated that a signaling loop exists between UB and SC. SC secrete signals to control RET expression and branching morphogenesis in UB cells, and adequate RET expression regulates normal SC patterning (Cullen-McEwen, Nephron Exp Nephrol, 2005). SC have also been suggested to promote the differentiation of MM (Das, Nature Cell Biology, 2013) and to contribute to vascular development (Sequeira-Lopez, Am J Physiol, 2014).

It has been demonstrated that an early stage embryonic kidney can be implanted in a mouse where it can develop into a mature and vascularized adult kidney (Rogers, Am J Physiol, 2001). It has further been shown that UB and MM cells have strong self-organizational potential and are able to form renal structures from single cell suspension in vitro (Unbekandt, Kid Intl, 2010), where embryonic kidneys were isolated at e11.5 and a single cell suspension was produced from UB and MM cells. The cells were re-aggregated by centrifugation and cultured in vitro as shown in FIG. 2, (reproduced from Unbekandt, Kid Intl, 2010). After 5-7 days, these aggregates contained simple renal structures (see also Ganeva, Organogenesis, 2011). Generation of tubular structures with a micropatterned gel from two dispersed UB-derived mouse cell lines has also been demonstrated (Hauser, J. Tissue Eng. Regen. Med., 2014; the disclosure of which is hereby incorporated by reference in its entirety).

These studies demonstrated that kidney progenitor cells (UB, MM, and SC) have a high self-organizing potential and are able to generate kidney structures. These experiments, however, also showed that the self-organization potential of the renal progenitor cells is limited. The kidney structures generated were disconnected and did not form the type of integrated, branched collecting duct structure necessary to excrete the filtered waste products (FIG. 3A-3B). Since a major function of the kidney is the filtration of blood and the draining of waste product through a centralized collecting duct system, this conventional re-aggregation method is not sufficient to develop into a functional organ.

There is therefore an urgent need for an improved system for kidney organogenesis to generate better functioning kidneys for treatment of ESRD. The present invention addresses this need.

SUMMARY OF THE INVENTION

The present invention relates to a kidney mold device, system, and method for generation of embryonic kidney organoids from kidney progenitor cells in vitro that can be implanted into a mammalian subject to form a functional kidney.

In one aspect, the invention is a kidney mold device for generating an embryonic kidney organoid. The kidney mold device comprises a ureteric bud (UB) cell chamber and a metanephric mesenchymal (MM) cell chamber, wherein the MM cell chamber is fluidly connected to the UB cell chamber. In one embodiment, the UB cell chamber is linearly shaped. In various embodiments, the MM cell chamber may have the shape of an ellipse, a bulb, or a circle. In various embodiments, the kidney mold device may be formed from a hydrogel or a plastic polymer. In one embodiment, the UB cell chamber and the MM cell chamber may be incorporated into a microfluidic device. In one embodiment, the invention relates to a precursor micromold comprising a plurality of channels for generating a UB tube from UB cells, wherein said channels are dimensioned such that the UB tubes formed in the channels will fit within the UB cell chamber of the kidney mold device.

In another aspect, the invention is a system for generating an embryonic kidney organoid. The system comprises a kidney mold device, kidney progenitor cells, growth media, and instructional material. In one embodiment, the system further comprises a precursor micromold. In another embodiment, the system further comprises a plug insertable into the MM cell chamber of the kidney mold device. In various embodiments, the plug comprises a dissolvable material selected from the group consisting of gelatin, hydrogel, and polymer. In various embodiments, the kidney progenitor cells may be induced from the group consisting of: embryonic cells, induced pluripotent stem cells, urine derived stem cells, or amniotic fluid stem cells. The kidney progenitor cells may be further differentiated towards the renal lineages of UB, MM, and stromal cells (SC).

In another aspect, the invention is a method for generating an embryonic kidney organoid. In one embodiment, the method comprises the steps of: seeding UB cells into a precursor micromold to generate a UB tube; transferring the UB tube into a kidney mold device UB cell chamber; generating a MM/SC aggregate or suspension; transferring the MM/SC aggregate or suspension into the kidney mold device MM cell chamber; and culturing the kidney mold device in growth media to generate an embryonic kidney organoid.

In another embodiment, the method comprises the steps of: inserting a plug into a kidney mold device MM cell chamber; seeding UB cells into the kidney mold device UB cell chamber to generate a UB tube; removing the plug by extraction or dissolution; generating a MM/SC aggregate or suspension; transferring the MM/SC aggregate or suspension into the kidney mold device MM cell chamber; and culturing the kidney mold device in growth media to generate an embryonic kidney organoid. In a further embodiment, the described methods comprise the step of implanting said embryonic kidney organoid into a mammalian subject so that it can mature into a functional kidney. In one embodiment, the embryonic kidney organoid is a human embryonic kidney organoid. In one embodiment, the MM/SC aggregate or suspension is suspended in a medium selected from the group consisting of collagen, agarose, polyacrylamide, and matrigel. In one embodiment, the MM/SC aggregate or suspension is aggregated into a sphere by overnight culture or by centrifugation. In one embodiment, extracellular matrix (ECM) of an embryonic or adult kidney is added to the MM/SC aggregate or suspension.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3, comprising FIG. 3A-3B, is an illustration depicting kidney drainage structures. FIG. 3A illustrates that the prior art technique of using a mixture of kidney progenitor cells fails to generate the branched drainage structure necessary to form a functional kidney. FIG. 3B illustrates the branched drainage structure present in a functional kidney.

FIG. 5, comprising FIG. 5A is a flowchart for generating an embryonic kidney organoid using a precursor micromold. FIG. 5B is a flowchart for generating an embryonic kidney organoid without a precursor micromold.

FIG. 6, comprising FIG. 6A is a perspective view of the cell chambers of one embodiment of the kidney mold device of the present invention having an elliptically-shaped MM cell chamber. FIG. 6B is a frontal view of one embodiment of the kidney mold device of FIG. 6A. FIG. 6C is a frontal view of another embodiment of the kidney mold device having a bulb-shaped MM cell chamber.

FIG. 8, comprising FIG. 8A conceptually illustrates how the UB tube grows into the MM/SC in the MM cell chamber. FIG. 8B is a bright field image of a UB tube that has been transferred into the UB cell chamber of a kidney mold device. FIG. 8C is an image of a UB tube branching into MM/SC. UB cells are immunostained green and MM/SC are immunostained orange. FIG. 8D-8E are images of further embryonic kidney organoid growth in a kidney mold device before the embryonic kidney organoid is ready to be implanted in an animal. UB cells are immunostained green and MM/SC are immunostained orange.

FIG. 9, comprising FIG. 9A shows several molds for forming precursor micromolds. FIG. 9B shows an embodiment of a hydrogel precursor micromold formed using the mold of FIG. 9A. FIG. 9C shows an embodiment of a plastic precursor micromold formed using the mold of FIG. 9A. FIG. 9D is a schematic depicting a precursor micromold with multiple chambers for UB cells.

FIG. 10, comprising FIG. 10A-10C, is a series of images depicting the use of a plug with a kidney mold device. FIG. 10A depicts one embodiment of a kidney mold device with a circular MM cell chamber. FIG. 10B depicts a circular gelatin plug next to the kidney mold device of FIG. 10A. FIG. 10C depicts a circular gelatin plug inserted into the MM cell chamber of the kidney mold device. As shown, the circular gelatin plug does not intrude into the UB chamber.

FIG. 11, comprising FIG. 11A depicts UB cells that have been seeded into the UB cell chamber and a MM/SC spherical aggregate seeded into the MM cell chamber of the kidney mold device. Prior to placing the MM/SC spherical aggregate, a plug was inserted in the MM cell chamber during UB cell culture and prevented UB cells from migrating into the MM cell chamber. FIG. 11B depicts the growth of UB cells within the UB cell chamber that has contacted the spherical MM cell aggregate.

FIG. 12, comprising FIG. 12A depicts an elliptical gelatin plug next to a T-shape kidney mold device. FIG. 12B depicts an elliptical gelatin plug inserted into the MM cell chamber of a T-shape kidney mold device.

FIG. 13, comprising FIG. 13A is a schematic that depicts a kidney mold device array comprising circular MM cell chambers fluidly connected to the midpoint of their respective UB cell chambers. FIG. 13B is a schematic that depicts a kidney mold device array comprising circular MM cell chambers fluidly connected to the terminus of their respective UB cell chambers.

FIG. 15, comprising FIG. 15A shows a UB cell chamber with a T-shape end fluidly connected to two MM cell chambers (here, there is one MM/SC aggregate in the right MM cell chamber). FIG. 15B is a close-up view of one MM/SC aggregate in a MM cell chamber. FIG. 15C-D depict a microfluidic kidney mold device comprising a central UB cell chamber with fluidly connected MM cell chambers running parallel on either side. FIG. 15C shows one MM/SC aggregate placed in the left MM cell chamber near a fluid connection. FIG. 15D shows two MM/SC aggregates placed in both MM cell chambers, with evidence of branching morphogenesis.

FIG. 16, comprising FIG. 16A-16C, is a series of images depicting the same microfluidic kidney mold device of FIG. 15 under different conditions. FIG. 16A is a bright field image of a kidney mold device seeded with UB cells and MM/SC aggregates. FIG. 16B is an image of the same kidney mold device immunostained for UB cells. The fluorescence indicates the presence of UB cells within the UB cell chamber with branching into the MM cell aggregate. FIG. 16C is an image of the same kidney mold device immunostained for MM cells. The fluorescence indicates the presence of MM cells within the MM cell chamber making contact with the UB cell branching.

DETAILED DESCRIPTION

Figure 1:
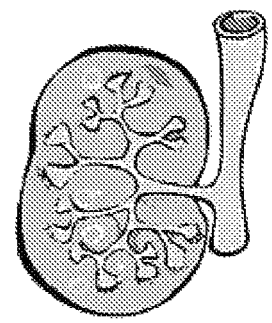
FIG. 1 is an illustration depicting the natural growth stages of an embryonic kidney.
Figure 1:
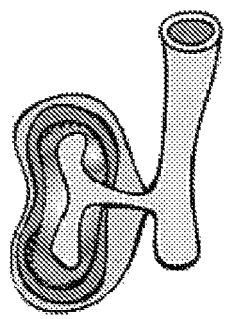
Figure 1:
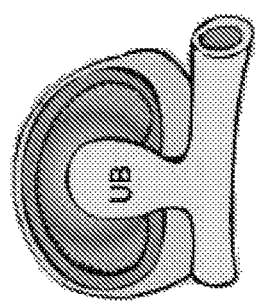
Figure 1:
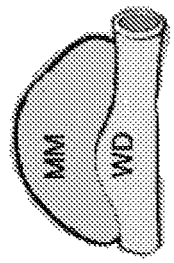
Figure 2:
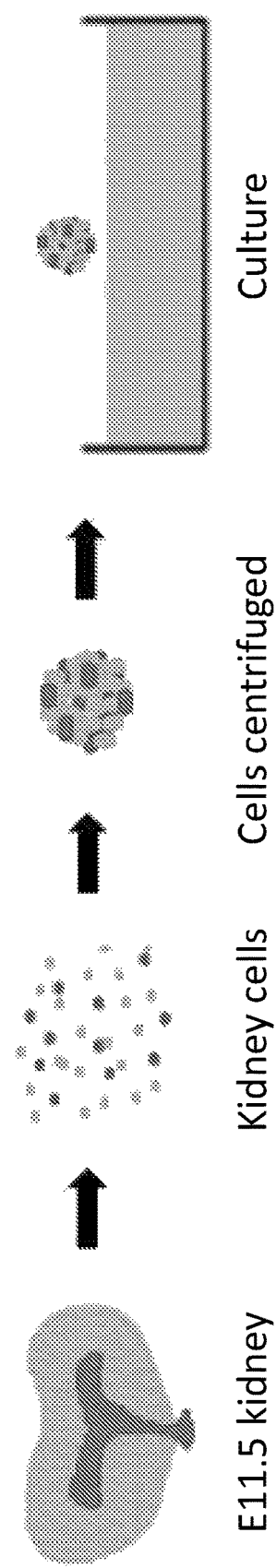
FIG. 2 is an illustration depicting a prior art attempt to generate a kidney using a mixture of progenitor kidney cells.

The present invention provides for a kidney mold device, system, and method for generation of embryonic kidney organoids from kidney progenitor cells in vitro that can be implanted into a mammalian subject to form a functional kidney.

In one embodiment, the kidney mold device comprises a ureteric bud (UB) cell chamber and a metanephric mesenchymal (MM) cell chamber. The UB cell chamber and MM cell chamber are fluidly connected. In one embodiment, the MM cell chamber is elliptical. In another embodiment, the MM cell chamber is circular. In one embodiment, the kidney mold device forms part of a microfluidic device. In various embodiments, the kidney mold device is supplemented with a precursor micromold. In various embodiments, the kidney mold device is supplemented with a plug.

The invention provides a system for generating an embryonic kidney organoid. In one embodiment, the system comprises a kidney mold device and kidney progenitor cells. The kidney progenitor cells may be any stem cell type that can be differentiated towards the renal lineages of UB cells, MM cells, and stromal cells (SC). In one embodiment, the system further comprises a precursor micromold. In one embodiment, the system further comprises a plug.

The invention provides a method for generating an embryonic kidney organoid. In one embodiment, the method comprises culturing kidney progenitor cells with the kidney mold device and system described herein. For example, in one embodiment, dispersed UB cells are first seeded into a precursor micromold to form a UB tube. The UB tube is transplanted into the UB cell chamber of the kidney mold device. Progenitor MM cells and SC are inserted into the MM cell chamber of the kidney mold device. As the UB tube grows into the MM and SC, an embryonic kidney organoid is formed with a functional drainage structure. After the embryonic kidney organoid has sufficiently developed, it is removed from the kidney mold device for implantation into a mammalian subject to allow for further development into a functional kidney. The device, system, and method of the present invention can be used to create kidneys for a number of mammalian subjects, including mice, rats, sheep, pigs, apes and humans.

DEFINITIONS

It is to be understood that the figures and descriptions of the present invention have been simplified to illustrate elements that are relevant for a clear understanding of the present invention, while eliminating, for the purpose of clarity, many other elements found in typical tissue engineering system and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

As used herein, "branching morphogenesis" encompasses the numerous cellular process involved in the formation of branched networks, including proliferation, survival/apoptosis, migration, invasion, adhesion, aggregation and matrix remodeling. The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

The term "contacting" as used herein can refer to bringing a disclosed composition, compound, or complex together with an intended target (such as, e.g., a cell or population of cells, a receptor, an antigen, or other biological entity) in such a manner that the disclosed composition, compound, or complex can affect the activity of the intended target (such as, e.g., a cell or population of cells, a receptor, an antigen, or other biological entity.), either directly (i.e., by interacting with the target itself), or indirectly (i.e., by interacting with another molecule, co-factor, factor, or protein on which the activity of the target is dependent). In an aspect, one or more agents can be contacted with a disclosed system or disclosed device, or cells contained therein.

"Differentiated" is used herein to refer to a cell that has achieved a terminal state of maturation such that the cell has developed fully and demonstrates biological specialization and/or adaptation to a specific environment and/or function. Typically, a differentiated cell is characterized by expression of genes that encode differentiation associated proteins in that cell. When a cell is said to be "differentiating," as that term is used herein, the cell is in the process of being differentiated.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the term "embryonic stem cell" refers to a cell that is derived from the inner cell mass of a blastocyst (e.g., a 4- to 5-day-old human embryo) and that is pluripotent. As used herein, the term "embryonic-like stem cell" refers to a cell that is not derived from the inner cell mass of a blastocyst. An embryonic-like stem cell is preferably pluripotent.

As used herein "growth factors" is intended the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), transforming growth factor (TGF-beta), hepatocyte growth factor (HGF), and bone morphogenetic protein at concentrations of between picogram/ml to milligram/ml levels.

As used herein, the term "growth medium" is meant to refer to a culture medium that promotes growth of cells. A growth medium will generally contain animal serum. In some instances, the growth medium may not contain animal serum.

As used herein, the term "induced pluripotent stem cell" or "iPS cell" is intended to indicate stem cell-like pluripotent cells which are derived from reprogrammed somatic cells (see for instance Takahashi K. et al. Cell 2007:131, 861-872; Yu J et al. Science 2007:318, 1917-1920; Feng, B et al. Cell Stem Cell 2009:4, 301-312). In many respects induced pluripotent stem cells possess the same properties as natural pluripotent stem cells, such as the expression of certain stem cell genes and proteins, chromatin methylation patterns, doubling time, embryoid body formation, teratoma formation, viable chimera formation, and potency and differentiability.

An "isolated cell" refers to a cell which has been separated from other s and/or cells which naturally accompany the isolated cell in a tissue or mammal.

As used herein, the "lineage" of a cell defines the heredity of the cell, i.e.; which cells it came from and what cells it can give rise to. The lineage of a cell places the cell within a hereditary scheme of development and differentiation.

The term "organoid" as used herein refers to an agglomeration of cells that recapitulates aspects of cellular self-organization, architecture and signaling interactions present in a native organ. The term "organoid" includes spheroids or cell clusters formed from suspension cell cultures.

As used herein, a "pluripotent cell" defines a less differentiated cell that can give rise to at least two distinct (genotypically and/or phenotypically) further differentiated progeny cells.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Kidney Mold Device

Figure 4:
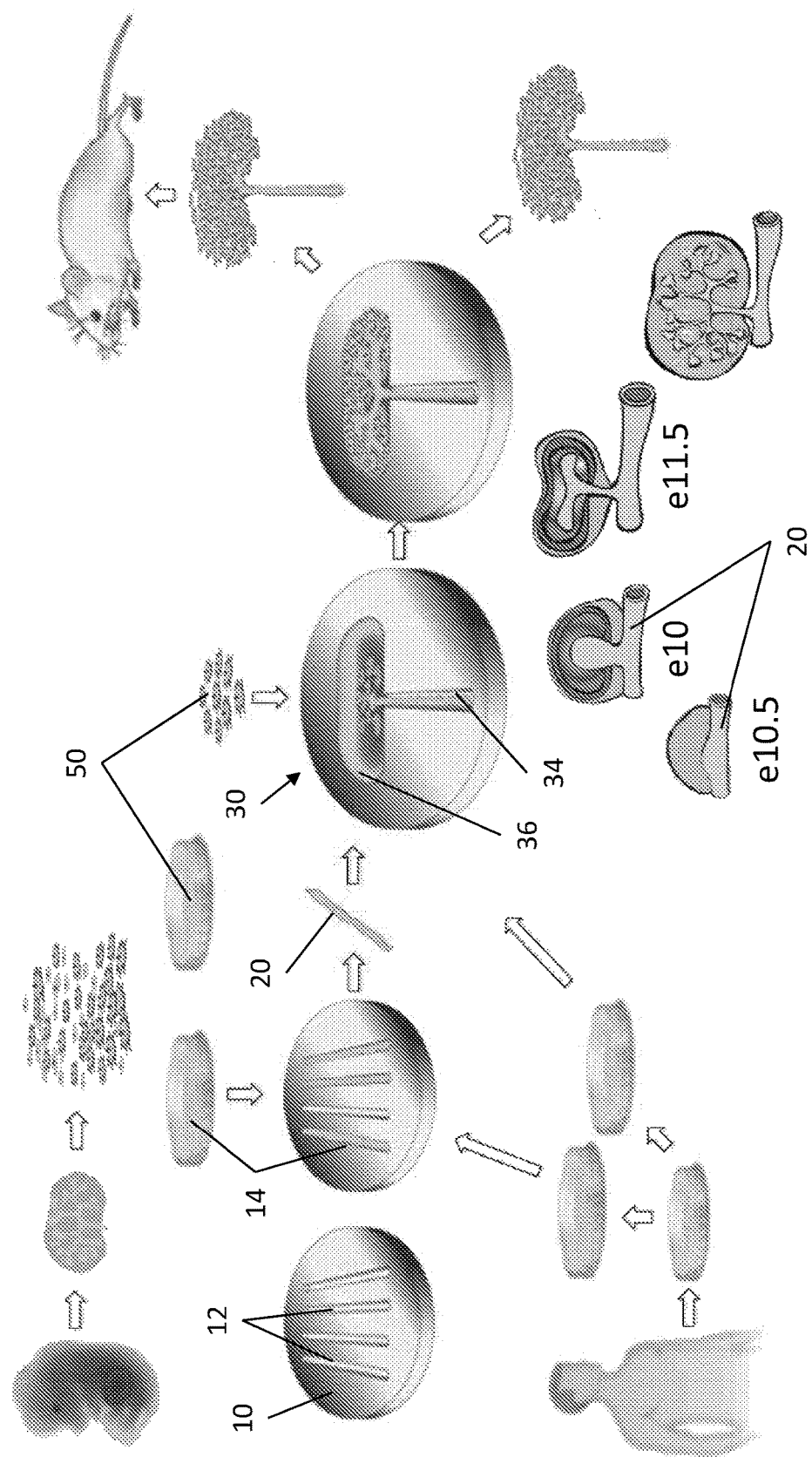
FIG. 4 is an illustration depicting one embodiment of the kidney mold device and method of the present invention.
Figures 6A, 6B, 6C:
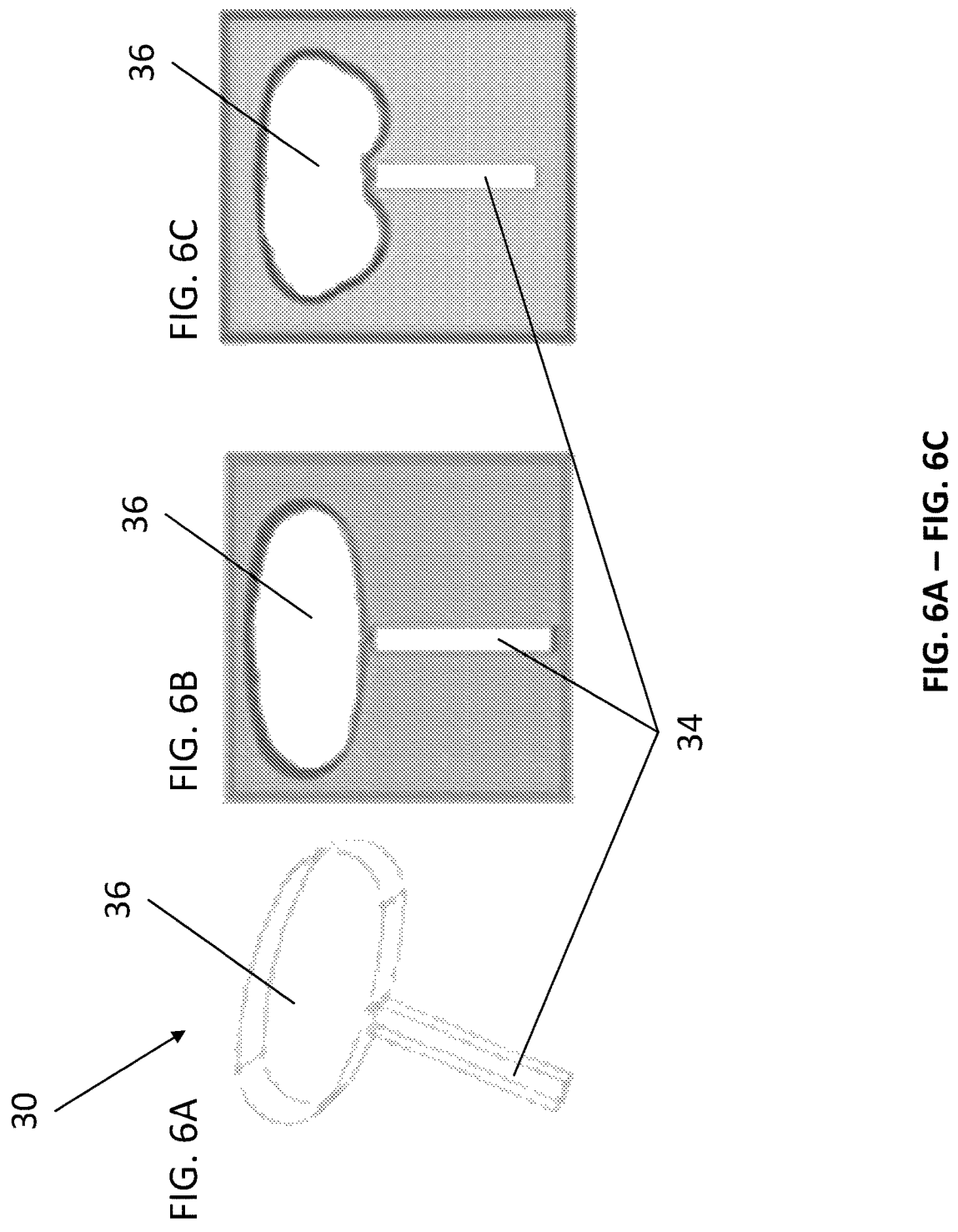
FIG. 6A-6C, is a schematic depicting various embodiments of the kidney mold device.

The present invention provides a kidney mold device for use with kidney progenitor cells to generate embryonic kidney organoids. Referring now to FIG. 4, one embodiment of a kidney mold device 30 is illustrated. The kidney mold device 30 comprises two types of cell chambers: a UB cell chamber 34 and a MM cell chamber 36. The shape and size of the chambers are designed to simulate the embryonic kidney environment. In some embodiments, the UB cell chamber 34 has a thin width and is linearly shaped to accommodate the dimensions of a UB tube. In some embodiments, the MM cell chamber 36 is substantially rounded to accommodate the dimensions of a cluster of MM and SC. Some non-limiting examples of MM cell chamber 36 shapes include an ellipse (FIG. 6B), a bulb (FIG. 6C), and a circle (FIG. 10A).

The UB cell chamber 34 is fluidly connected to the MM cell chamber 36. The fluid connection between UB cell chamber 34 and MM cell chamber 36 reflects the spatiotemporal development of the embryonic kidney at embryonic stage e11. Specifically, the fluid connection between UB cell chamber 34 and MM cell chamber 36 is designed to simulate the time point (e11) at which UB cells, attracted by growth factors, branch into the metanephric mesenchyme composed of MM cells and SC.

In one embodiment, the MM cell chamber 36 is fluidly connected to the terminus of the UB cell chamber 34 to form a T-shape, such as in FIG. 4. In another embodiment, the MM cell chamber 36 is fluidly connected to the midpoint of the UB cell chamber 34, such as in FIG. 13A. In various embodiments, the MM cell chamber 36 may be fluidly connected to any point along the length of the UB cell chamber 34, such as in FIG. 10A. In various embodiments, a plurality of MM cell chambers 36 may be fluidly connected to any point along the length of UB cell chamber 34, such as in FIG. 15D.

Figure 13A:
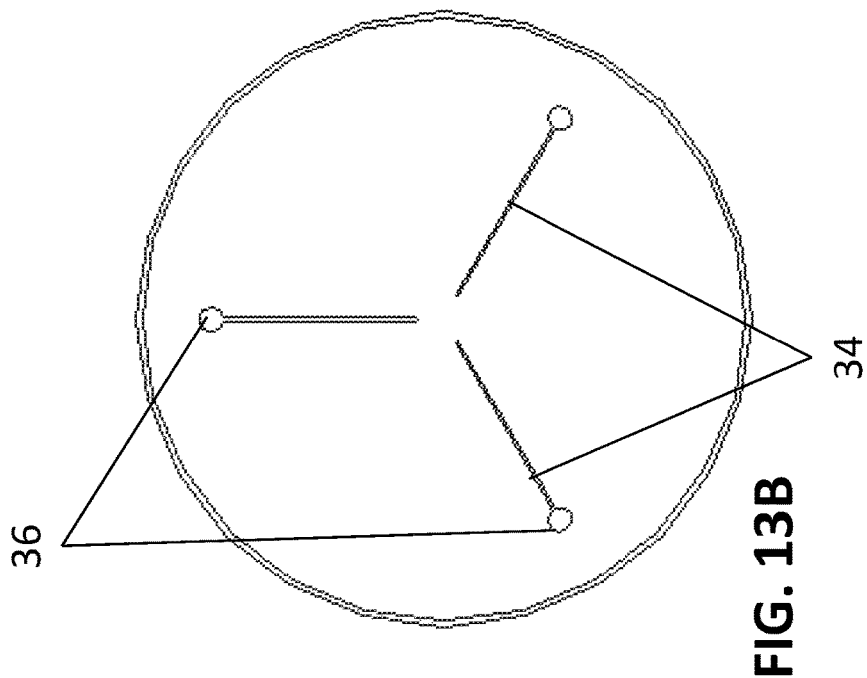
FIG. 13A-13B, is a series of schematics depicting different embodiments of kidney mold device arrays.
Figure 13B:
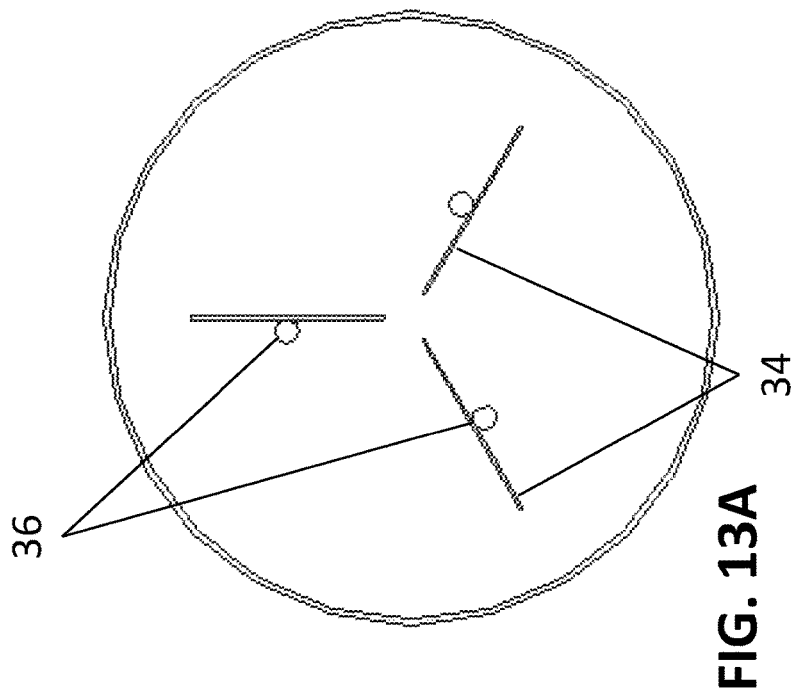
Figure 14:
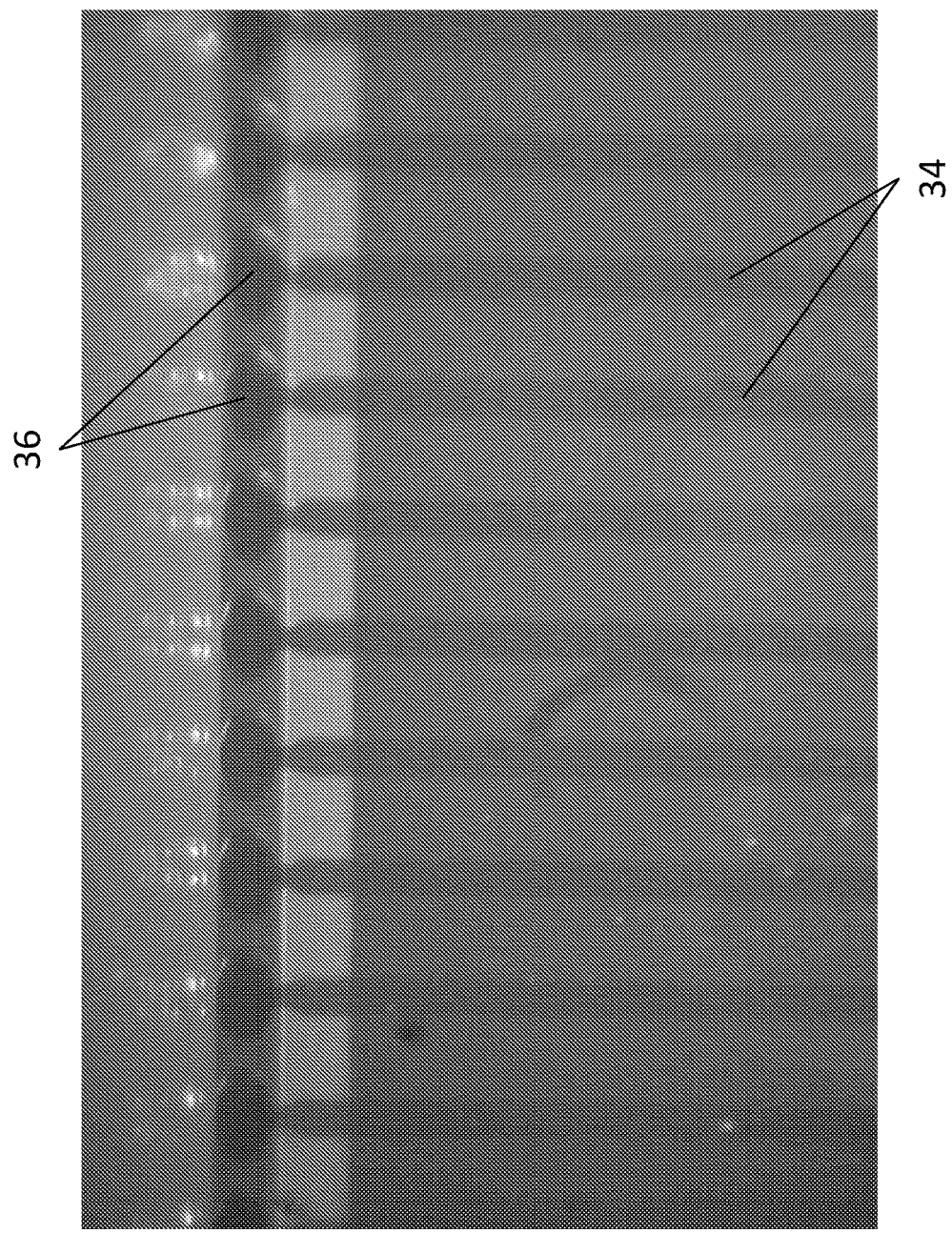
FIG. 14 is an image depicting a microfluidic kidney mold device. MM cell chambers and UB cell chambers are arranged in parallel. The MM and UB cell chambers are independently connected with filling channels to allow for seeding of their respective cells.

In one embodiment, a plurality of kidney molds may be arranged as an array on a single device. Referring now to FIG. 13A-13B, two arrays are depicted. FIG. 13A illustrates a kidney mold array comprising three kidney molds with MM cell chambers 36 fluidly connected to the midpoint of their respective UB cell chambers 34. FIG. 13B illustrates a kidney mold array comprising three kidney molds with MM cell chambers 36 fluidly connected to the terminus of their respective UB cell chambers 34. In one embodiment, the kidney mold device is a microfluidic kidney mold device. Referring now to FIG. 14, a microfluidic kidney mold device is depicted. UB cell chambers 34 are arranged in parallel, and each UB cell chamber 34 is fluidly connected at its terminus to a MM cell chamber 36. The MM and UB cell chambers are independently connected with filling channels to allow for seeding of their respective cells.

The kidney mold device 30 may be produced from any one of a number of different materials that form polymers. A list of non-limiting examples that may be used includes hydrogels, such as agarose or gelatin, or plastic polymers, such as PDMS, latex or polyacrylamide gels. In certain embodiments, hydrogels can be used in different concentrations to generate different desired surface tensions. Further, all or any portion of a hydrogel kidney mold device can be modified by coating with single extracellular matrix proteins (e.g. collagen I, collagen IV, fibronectin, laminin or matrigel, etc.) or a complex mixture of extracellular matrix proteins generated from, for example, decellularized embryonic or adult kidneys, or can be modified by coating (or covalent binding) with molecules that change the hydrophobicity of the kidney mold.

Figure 7:
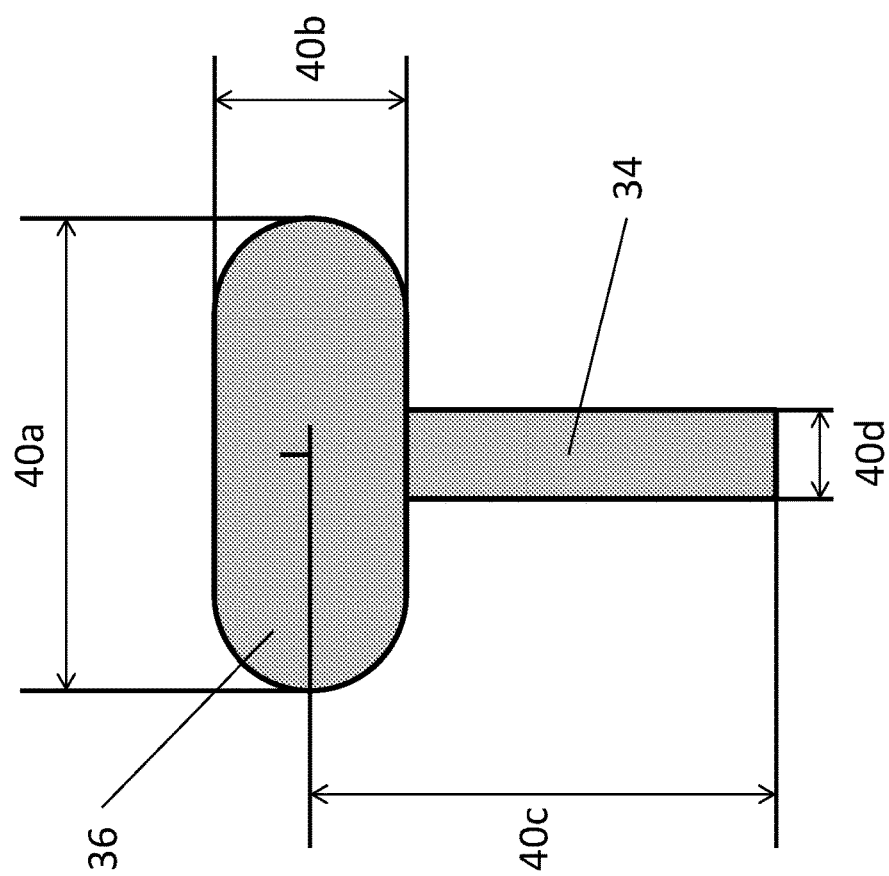
FIG. 7 is a schematic depicting the dimensions of one embodiment of the kidney mold device.

Referring now to FIG. 7, an exemplary set of dimensions for one embodiment of the kidney mold device 30 is illustrated. For example, the length 40*a* of the MM cell chamber 36 may be between 400 and 1000 µm, while the width 40*b* of the MM cell chamber 36 may be between 250 and 500 µm. The length 40*c* of the UB cell chamber 34 may be between 800 and 1250 µm while the width 40*d* of the UB cell chamber may be between 50 and 200 µm. The depth of the UB cell chamber 34 and MM cell chamber 36 may vary between 50 to 400 µm. As those of skill in the art will recognize, the dimensions and overall size of the kidney mold device 30 will vary depending upon the expected size of the embryonic kidney for the particular mammalian species chosen.

Precursor Micromold

Figure 9A:
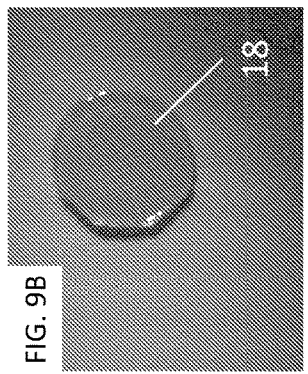
FIG. 9A-9D, is a series of images depicting precursor micromold molds and the precursor micromold itself.

In one embodiment, the use of the kidney mold device is supplemented with a precursor micromold. Referring now to FIG. 4, a precursor micromold 10 having a plurality of channels 12 is shown. The precursor micromold 10 may be formed from a plastic polymer, such as a polydimethylsiloxane (PDMS) polymer. For example, the PDMS polymer can be produced using the Sylgard 184 Silicon Elastomer Kit (Dow Corning Corp., Midland, Mich., USA) according to manufacturer's recommendations. To make a PDMS polymer micromold, polymer reagents are mixed in a ratio of 10:1 and homogenized by stirring. The mixture is then poured into forms in mold 16, as shown in FIG. 9A, and exposed to a 10% vacuum for 10 minutes to remove trapped air bubbles. The PDMS polymer is cured by baking at 85° C. for 2 hours. In one embodiment, channels 12 are produced by photocatalytic generated lithography techniques. After precursor micromold 10 is removed from mold 16 as shown in FIG. 9C, the PDMS polymer precursor micromold 10 is washed in 70% ethanol, rinsed in PBS, and air-dried under sterile conditions.

Figure 9B:
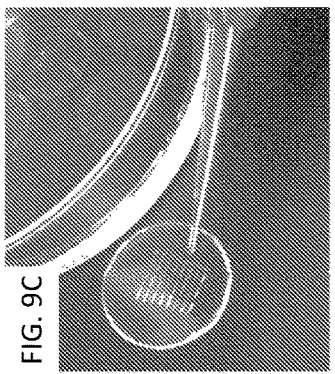
Figure 9C:
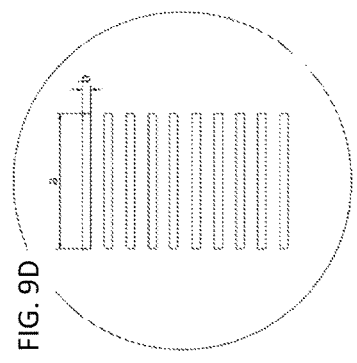
Figure 9D:
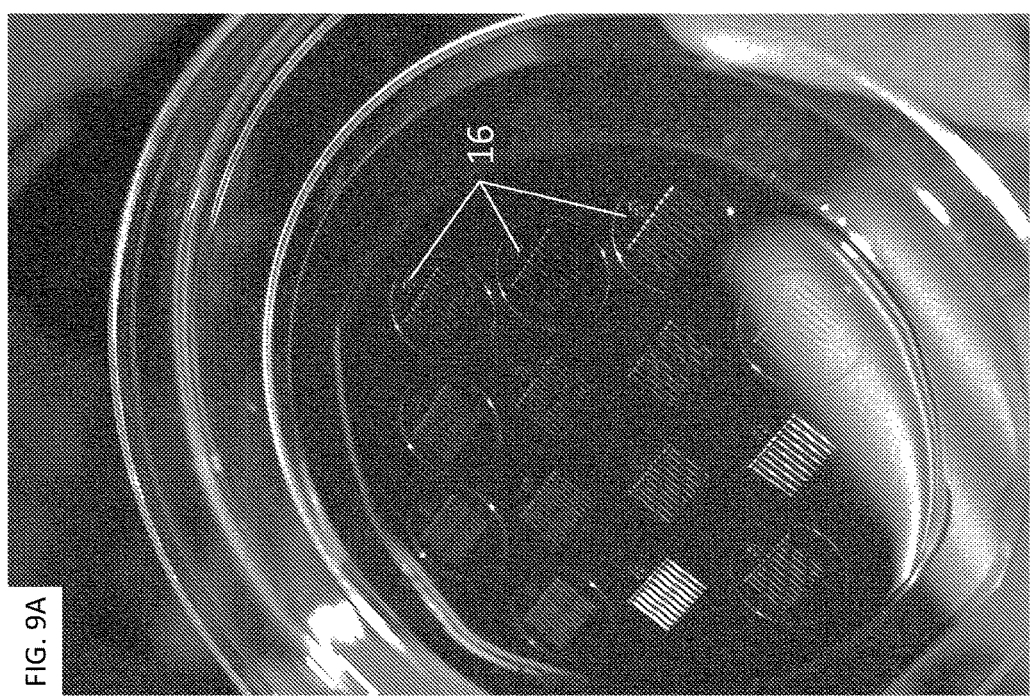

In another embodiment, a hydrogel based precursor micromold 18 can be used, as shown in FIG. 9B. To make such a hydrogel based precursor micromold 18, a liquid hydrogel solution is prepared by melting agarose (1-4%) in serum free growth media. After the liquid agarose solution is cooled, about 10-12 milliliters of the agarose solution is pipetted into mold 16 and left for polymerization. All of these steps are carried out using sterile techniques. Once the hydrogel has polymerized, the hydrogel precursor micromold 18 is removed from mold 16 in a manner similar to that shown in FIG. 9C. Other hydrogels, such as polyacrylamide or fibronectin can alternatively be used to make a hydrogel based precursor micromold 18.

Plug

Figure 12A:
FIG. 12A-12B, is a series of images depicting the use of a plug with a T-shape kidney mold device.
Figure 12B:

In one embodiment, the use of the kidney mold device is supplemented with a plug. Referring now to FIGS. 10C and 12B, the two chambers of the kidney mold device 30 can be divided by plug 52. In various embodiments, plug 52 may be made from gelatin or a different hydrogel with or without extracellular matrix proteins. In one embodiment, plug 52 is dissolvable, such as a dissolvable hydrogel or polymer. In various embodiments, plug 52 may comprise additional ECM. Plug 52 forms a physical barrier in the fluid connection between UB cell chamber 34 and MM cell chamber 36 but does not intrude into UB cell chamber 34. Plug 52 prevents physical entry of the MM cell chamber 36 by UB cells. In one embodiment, plug 52 is shaped to fit within the confines of the MM cell chamber 36. In another embodiment, plug 52 comprises a length of material that is coiled, such that the coiled material is compressible and expands to conform to the confines of the MM cell chamber 36 after insertion.

Kidney Progenitor Cells

As described herein, the invention relates to the use of a kidney mold device with kidney progenitor cells to generate embryonic kidney organoids that can be implanted into a mammalian subject to form a functional kidney. The primary kidney progenitor cells used are ureteric bud (UB) cells, metanephric mesenchymal (MM) cells, and stromal cells (SC).

The kidney progenitor cells may be any stem cell type that can be differentiated towards the renal lineages of UB, MM, and SC. For example, the kidney progenitor cells may be germ-line stem cells, fat tissue derived stem cells, or embryonic cells. In one embodiment, the kidney progenitor cells are induced pluripotent stem cells (iPSCs). iPSCs are a type of pluripotent stem cell artificially derived from a non-pluripotent cell, typically an adult somatic cell, which can be, but are not limited to, fibroblasts from skin or kidney cells from urine. Kidney progenitor cells that are iPS cells are differentiated towards the renal lineages of UB, MM, and SC. iPS cells may be sourced from the mammalian subject in whom an embryonic kidney organoid is to be implanted. iPS cells may be sourced from a stem cell bank and matched to the human leukocyte antigen (HLA) type of the mammalian subject in whom an embryonic kidney organoid is to be implanted.

In one embodiment, the kidney progenitor cells are urine derived stem cells (USC). Urine stem cells may be collected from any animal that produces urine, including humans. In some embodiments of the present invention, urine stem cells are collected from the urine of a mammal. For example, USC may be collected from the urine of a dog, cat, pig, cow, horse, monkey or human. In particular embodiments, USC are obtained from the urine of a human. USC may be collected from any portion of the urinary tract. In some embodiments, USC are collected from the upper urinary tract (UUT) (kidneys, ureter), e.g., via a catheter such as a nephrostomy catheter. In other embodiments, USC are collected from the lower urinary tract (bladder, urethra), via a catheter such as a urinary catheter. Further examples of methods and apparatuses for isolating cells from biological fluids may be found in, e.g., U.S. Pat. No. 5,912,116; U.S. Patent Application No. 20040087017; U.S. Patent Application No. 20020012953; and WO 2005/047529.

Kidney progenitor cells that are urine derived stem cells are differentiated towards the renal lineages of UB, MM, and SC. Urine derived stem cells may be sourced from the mammalian subject in whom an embryonic kidney organoid is to be implanted. Urine derived stem cells may be sourced from a donor and matched to the HLA type of the mammalian subject in whom an embryonic kidney organoid is to be implanted.

In one embodiment, the kidney progenitor cells are amniotic fluid stem cells (AFSCs). AFSCs useful for carrying out the present invention are known and have been described (for example, PCT Application WO 03/042405 to Atala and DeCoppi; In't Anker, P. S., et al., Amniotic fluid as a novel source of mesenchymal stem cells for therapeutic transplantation. Blood, 2003. 102(4): p. 1548-9; Prusa, A. R., et al., Oct-4-expressing cells in human amniotic fluid: a new source for stem cell research? Hum Reprod, 2003. 18(7): p. 1489-93; Kaviani, A., et al., The amniotic fluid as a source of cells for fetal tissue engineering. J Pediatr Surg, 2001. 36(11): p. 1662-5; Prusa, A. R. and M. Hengstschlager, Amniotic fluid cells and human stem cell research: a new connection. Med Sci Monit, 2002. 8(11): p. RA253-7). In general, AFSCs are cells, or progeny of cells, that are found in or collected primarily from mammalian amniotic fluid, but may also be collected from mammalian chorionic villus or mammalian placental tissue.

Kidney progenitor cells that are amniotic fluid stem cells are differentiated towards the renal lineages of UB, MM, and SC. Amniotic fluid stem cells may be sourced from the mammalian subject in whom an embryonic kidney organoid is to be implanted. Urine derived stem cells may be sourced from a donor and matched to the HLA type of the mammalian subject in whom an embryonic kidney organoid is to be implanted.

Kidney Generation System

The present invention provides a system for the generation of a kidney. The system is a combination of individual devices and compositions useful for carrying out the method of the invention, wherein the devices and compositions are optimized for use together in the method. Thus, the system can include one or more of the following: kidney mold device, kidney progenitor cells, growth media, and the like. In one embodiment, the system further comprises precursor micromolds. In another embodiment, the system further comprises plugs. In another embodiment, the system comprises microfluidic kidney mold devices.

A composition comprises an individual component or a blend of components for at least one step of a method of the invention. The invention comprises any system that can be assembled from a combination of any device and composition of the invention, and any novel device and composition that is used in a system or method of the invention. Alternatively, a system may be assembled from a single device or composition in a convenient use format, e.g., pre-formed ureteric buds and metanephric mesenchyme, and may optionally include a set of instructions for use of the device or composition.

Method

As described and demonstrated herein, the kidney mold device of the present invention controls the initial interaction between UB and MM/SC in a manner that allows the generation of embryonic kidney tissue in vitro with the potential to drain urine in a properly functioning excretory organ. Accordingly, the kidney mold device mimics the anatomy of the embryonic kidney insofar as it initially separates UB and MM/SC to allow a controlled interaction of these cell types.

Figure 5A:
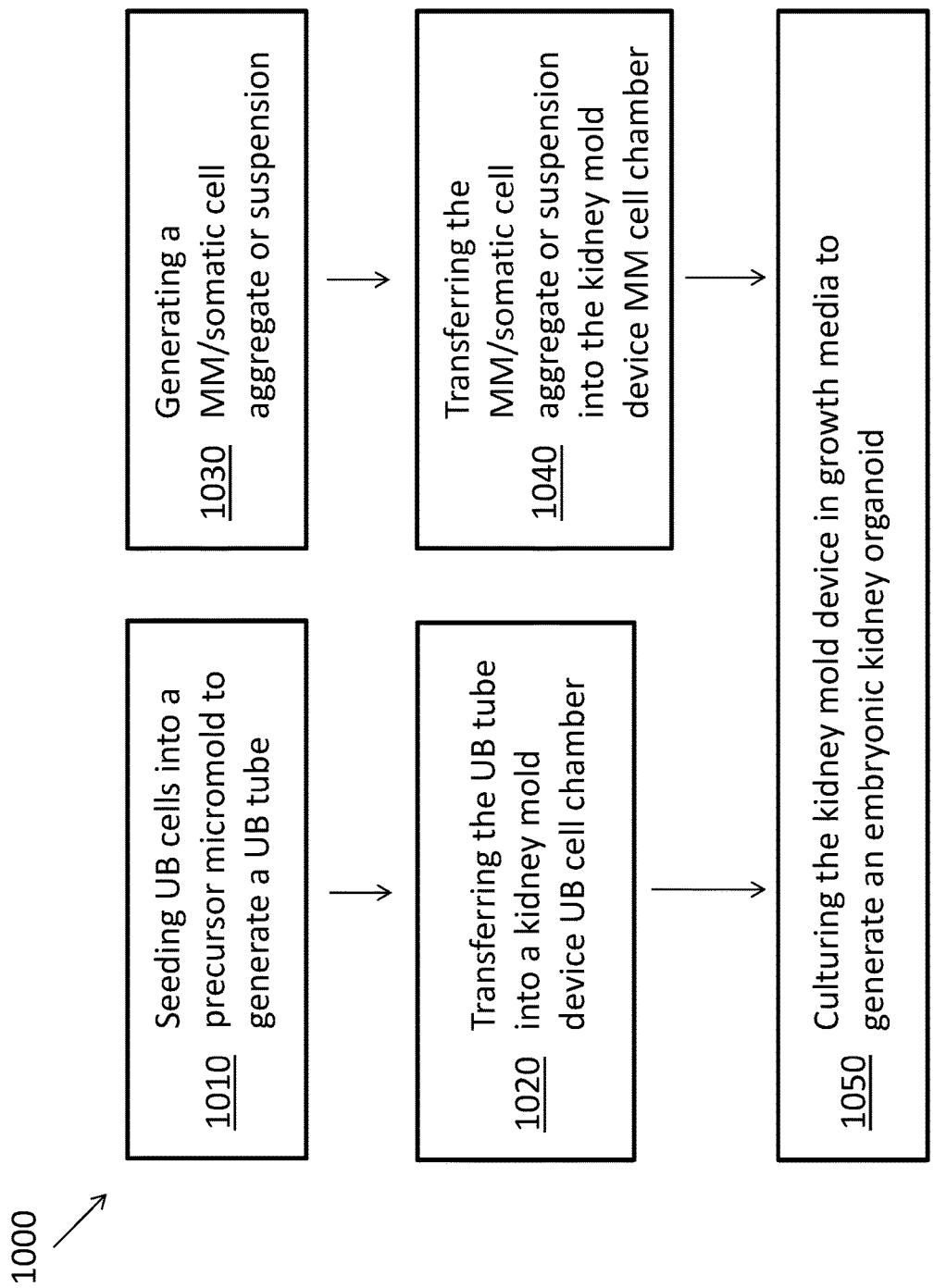
FIG. 5A-5B, are flowcharts illustrating exemplary methods for generating embryonic kidney organoids.

Referring now to FIG. 5A, a flowchart illustrating an exemplary method 1000 for generating an embryonic kidney organoid of the present invention is depicted. Method 1000 comprises seeding UB cells into a precursor micromold to generate a UB tube 1010, then transferring the UB tube into a kidney mold device UB cell chamber 1020. Method 1000 also comprises generating a MM/SC aggregate or suspension 1030, then transferring the MM/SC aggregate or suspension into the kidney mold device MM cell chamber 1040. The kidney mold device is then cultured in growth media to generate an embryonic kidney organoid 1050.

Referring now to FIG. 4, the abovementioned method 1000 is illustrated. UB cells 14 are seeded into one the channels 12 of precursor micromold 10 to generate UB tube 20. UB tube 20 is then transferred into UB cell chamber 34 of kidney mold device 30, such as by pipetting or microforceps. MM/SC aggregate or suspension 50 is transferred into MM cell chamber 36 of kidney mold device 30. Kidney mold device 30 is cultured in growth media to generate an embryonic kidney organoid suitable for implantation.

Figure 5B:
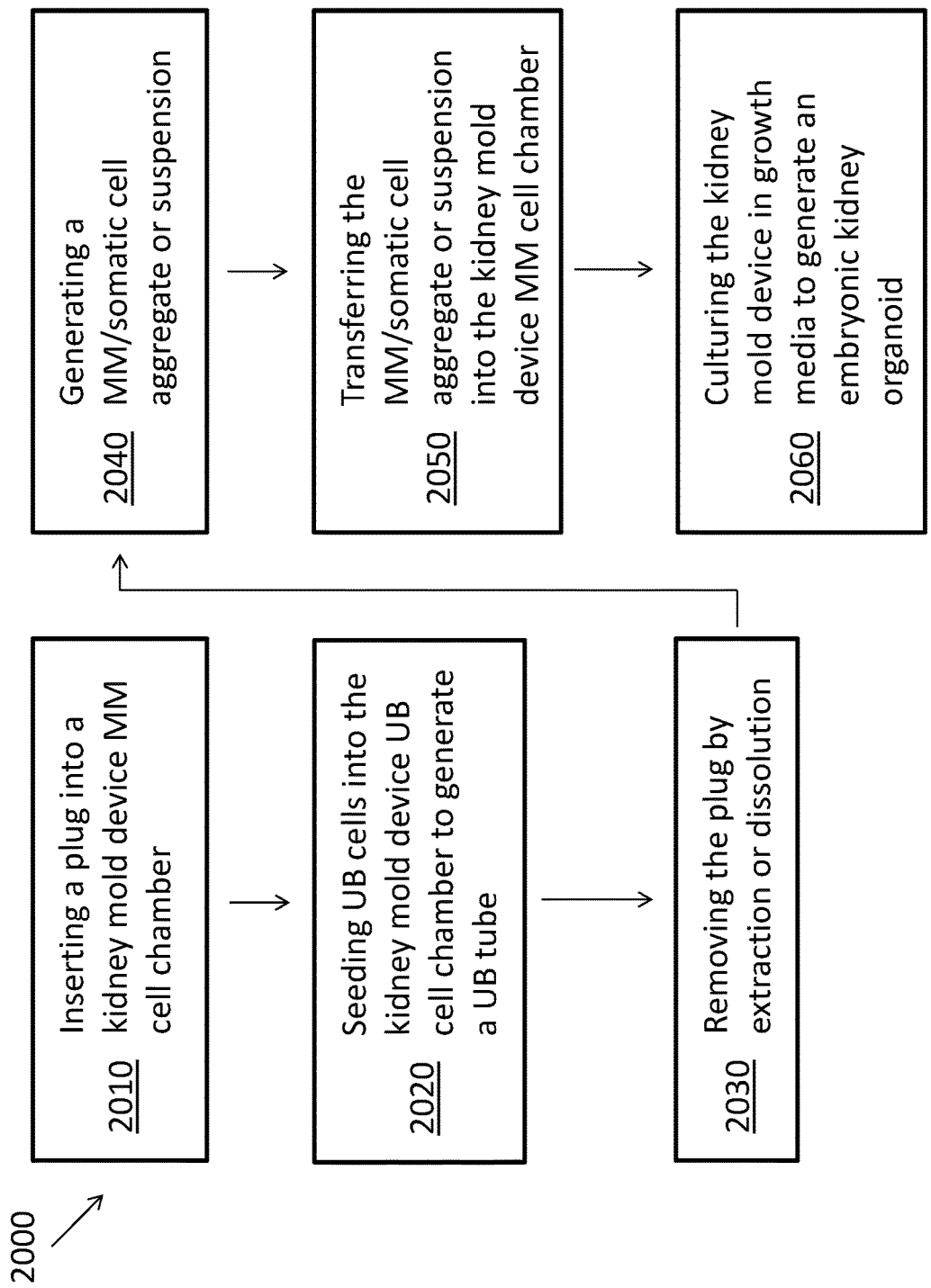

Referring now to FIG. 5B, a flowchart illustrating an exemplary method 2000 for generating an embryonic kidney organoid of the present invention is depicted. Method 2000 comprises inserting a plug into a kidney mold device MM cell chamber 2010 first, then seeding UB cells into the kidney mold device UB cell chamber to generate a UB tube 2020. The plug is then removed by extraction or dissolution 2030. Method 2000 further comprises generating a MM/SC aggregate or suspension 2040, then transferring the MM/SC aggregate or suspension into the kidney mold device MM cell chamber 2050. The kidney mold device is then cultured in growth media to generate an embryonic kidney organoid 2060.

In one embodiment, UB cells may be seeded in suspension in a layer of liquid hydrogels, such as collagen I, agarose, polyacrylamide or matrigel, etc. In another embodiment, the ECM components from adult or embryonic kidneys can be used in the UB cell suspension to stimulate differentiation and branching. After approximately 24 to 48 hours of incubation at, for example, 37° C. in the presence of $O_2/CO_2$ (95%/5%), the UB cells polarize and form a UB tube. The UB tube may be held in place using a highly concentrated solution (3-6%) of liquid hydrogels, such as collagen I, agarose, polyacrylamide, or matrigel. When transferring the UB tube into the UB cell chamber, the UB tube may be placed with one end reaching into the MM cell chamber. To prevent the other end of the UB tube from branching, branching inhibiting substances, such as Tgf-β, can be applied.

In one embodiment, MM/SC may be suspended in liquid hydrogels, such as collagen I (0.5-1%), agarose (0.4-0.8%), polyacrylamide (0.5-1%), or matrigel (30-80%). In another embodiment, the ECM components from adult or embryonic kidneys can be used in the MM/SC suspension to stimulate differentiation and branching. In one embodiment, the MM/SC may be prepared as a spherical aggregate. The spherical aggregates may be formed by methods known in the art, such as by overnight culture in round bottom well plates or by centrifugation.

The time interval between the placement of the UB tube in the UB cell chamber and the placement of the MM/SC aggregate or suspension in the MM cell chamber should be kept short in order to prevent damage to the UB tube cells extending into the MM cell chamber. Care should also be taken to avoid contamination of MM/SC into the UB cell chamber in order to prevent branching of the UB tube where it is not wanted.

After polymerization of the liquid hydrogel that suspends the MM/SC, the UB tube and MM/SC in the kidney mold are submerged in growth media and cultured in vitro at around 37° C. under $O_2/CO_2$ (95%/5%). Growth media used is, for example, DME/F12 with 10% fetal bovine serum or conditioned media from a MM derived cell line (BSN Sakurai H, An in vitro tubulogenesis system using cell lines derived from the embryonic kidney shows dependence on multiple soluble growth factors. PNAS 1997, 94(12):6279-6284. Growth media can be complemented with suitable growth factors. If a hydrogel based kidney mold device is used, the kidney mold device can be placed on a metal screen and incubated on the surface of the growth media, similar to well-known organ culture techniques (see, Grobstein, Nature, 1953; Grobstein, Exp. Cell Res., 1956; Grobstein, Exp. Cell Res., 1957).

In one embodiment, the embryonic kidney organoid can be prepared for vascularization prior to implanting into a mammalian subject. In a non-limiting example, the embryonic kidney organoid can be incubated in vascular endothelial growth factor (VEGF) for 3 hours before removal from the kidney mold device and implanting into a mammalian subject.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: UB Tube Branching in a T-Shape Kidney Mold Device

Figures 8A, 8B, 8C, 8D, 8E:
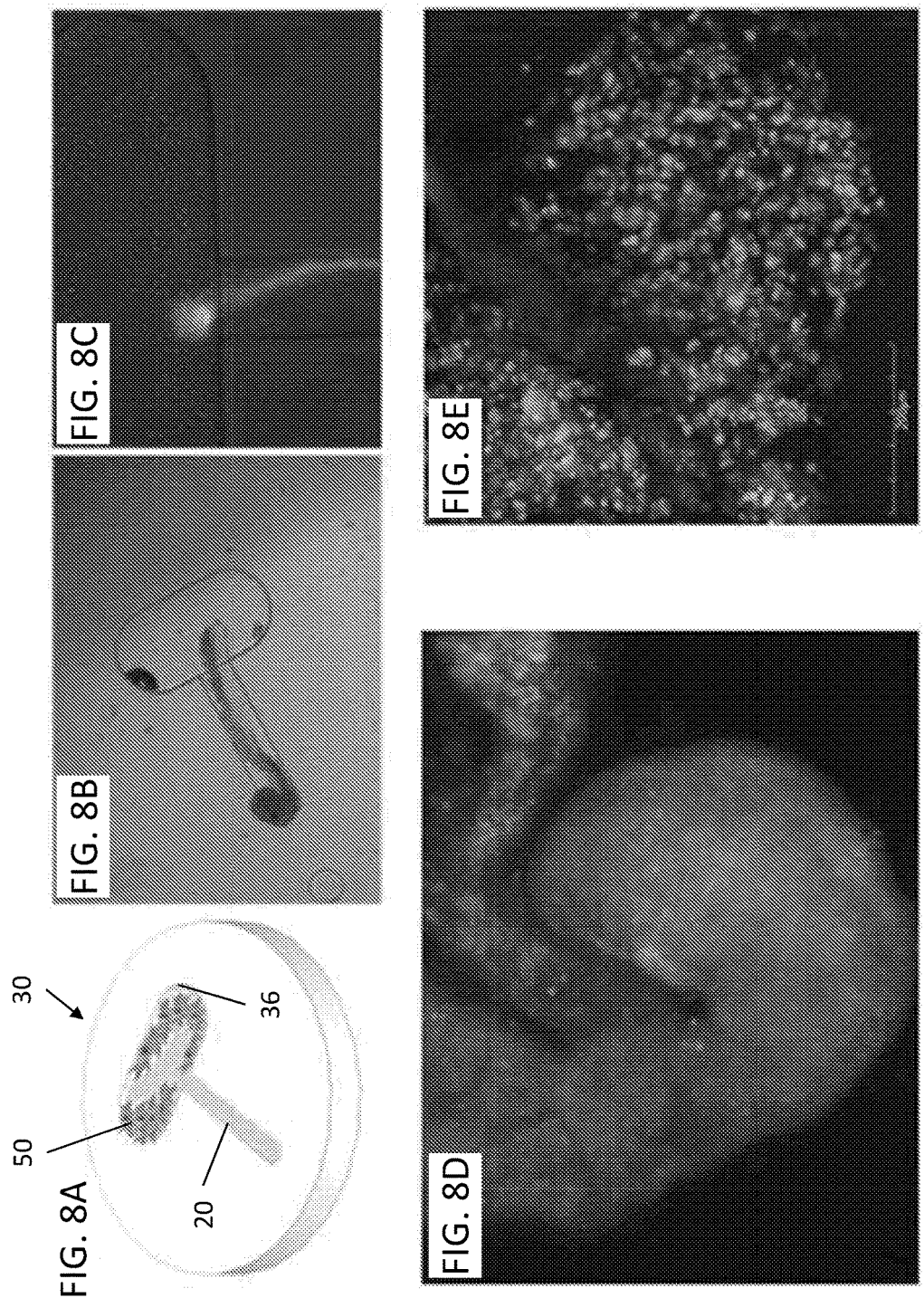
FIG. 8A-8E, is a series of images depicting different stages of embryonic kidney organoid development.

FIG. 8A-E depict the UB tube 20 growing into MM/SC 50 in the MM cell chamber 36 with branching morphogenesis. In FIG. 8B, the end of UB tube 20 that is not in contact with the MM cell chamber remains unbranched. When sufficient branching morphogenesis of the UB tube 20 has occurred within the MM cell chamber 36, as illustrated in FIGS. 8D and E, the embryonic kidney organoid can be removed from the kidney mold by pipette or forceps and implanted into a mammalian subject for further development.

Example 2: Plug Use in a Circular Kidney Mold Device

Figure 11A:
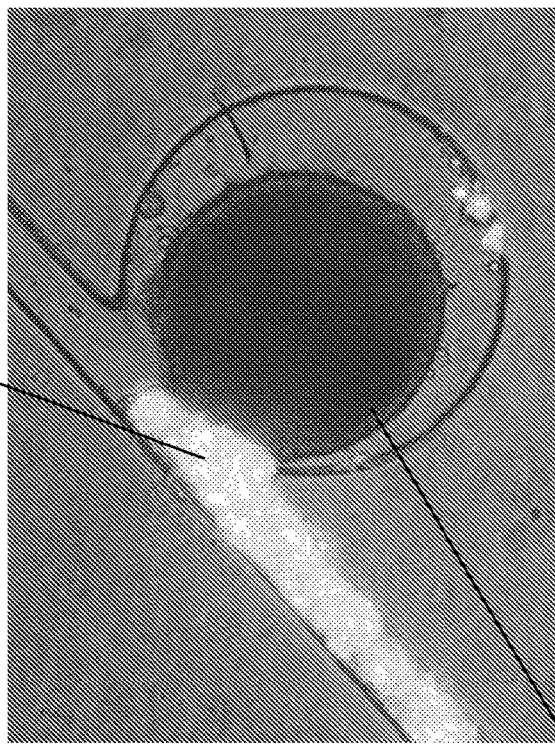
FIG. 11A-11B, is a series of images depicting the seeding of UB cells and MM/SC in a kidney mold device with the aid of a plug.
Figure 11B:
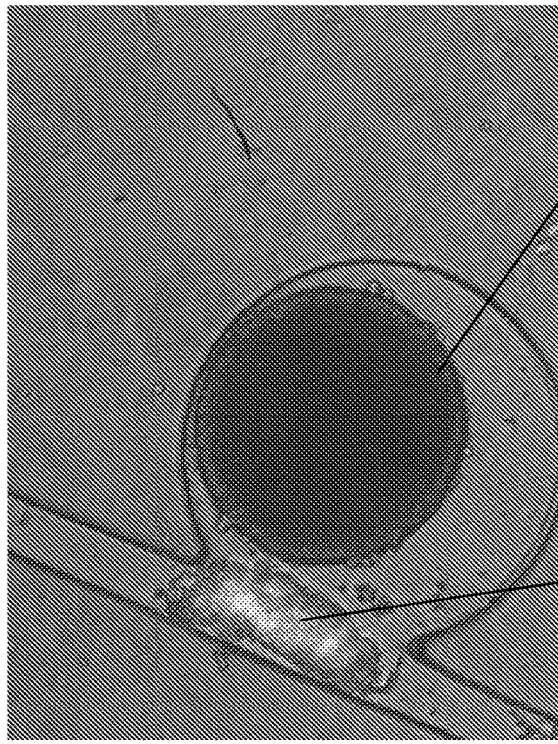

FIG. 11A-11B depict the generation of an embryonic kidney organoid without using a precursor micromold. UB cells were seeded directly into the UB cell chamber of a kidney mold device having a plug in the MM cell chamber. FIG. 11A shows the kidney mold device with a rudimentary UB tube (immunostained green) after the plug has dissolved, with a MM/SC aggregate placed in the MM cell chamber. Note that in FIG. 11A, no UB cells are present in the MM cell chamber due to the use of the plug. FIG. 11B shows that branching morphogenesis has begun with the UB tube extending into the MM/SC aggregate.

Example 3: Microfluidic Kidney Mold Variations

Figure 15A:
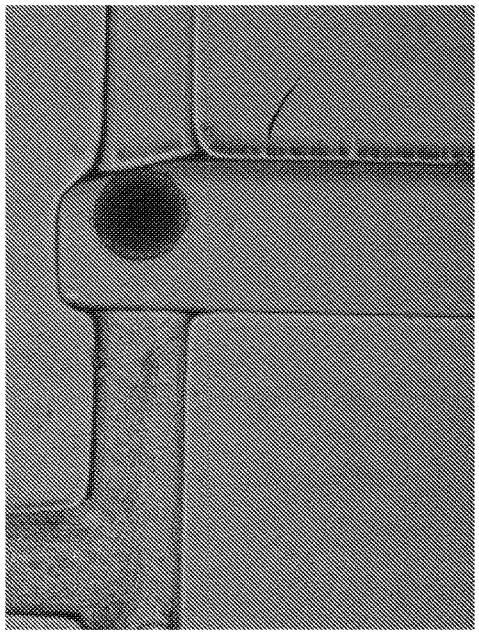
FIG. 15A-15D, is a series of images depicting the layout of a microfluidic embodiment of the kidney mold device.
Figure 15B:
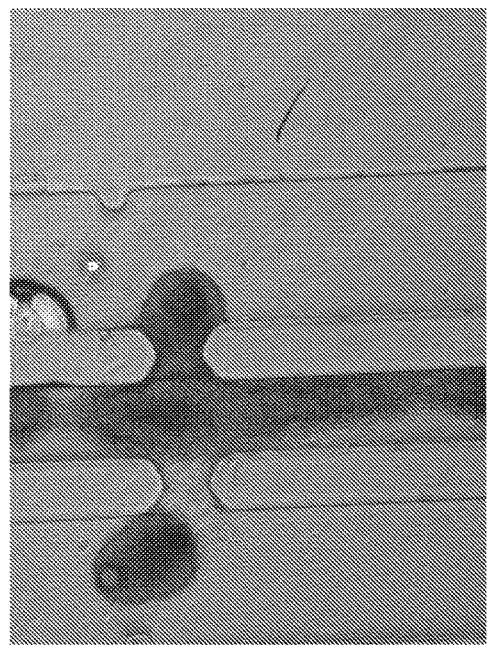

FIG. 15A-15B depict the use of microfluidic kidney mold variations to generate embryonic kidney organoids. FIG. 15A depicts a microfluidic kidney mold variation comprising a central UB cell chamber with two MM cell chambers fluidly connected at its terminus, one on either side. UB cells have been seeded into the UB cell chamber, and a MM/SC spherical aggregate has been transferred into the right MM cell chamber. FIG. 15B depicts a closer view of the MM/SC spherical aggregate in a microfluidic kidney mold MM cell chamber.

Figure 15C:
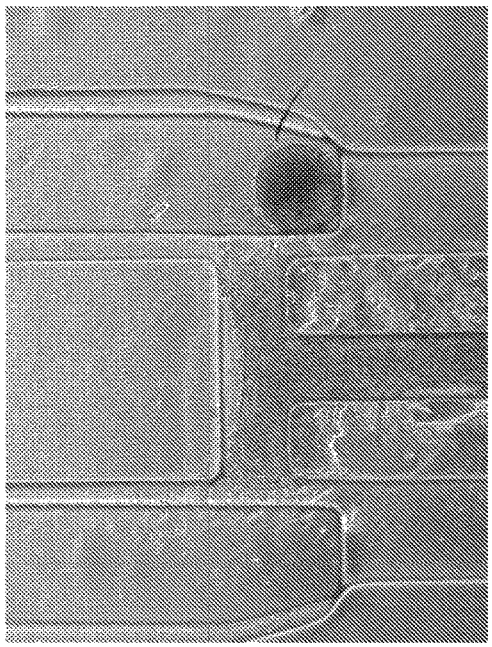
Figure 15D:
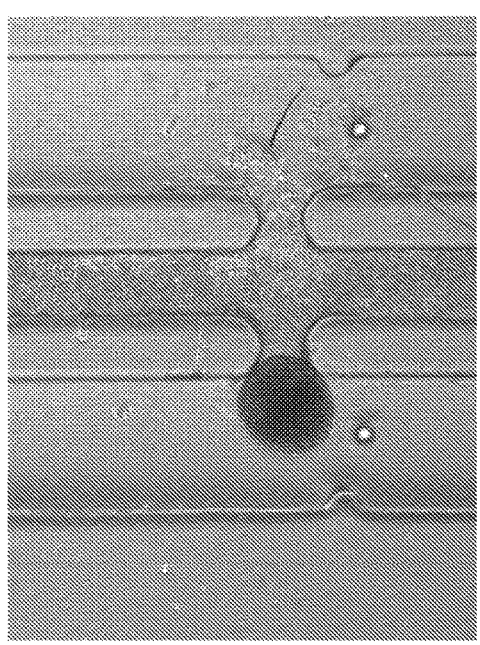

FIG. 15C depicts a microfluidic kidney mold variation comprising a central UB cell chamber with two linear MM cell chambers fluidly connected in parallel, one on either side. UB cells have been seeded into the UB cell chamber, and a MM/SC spherical aggregate has been transferred into the left MM cell chamber near the fluid connection. FIG. 15D depicts the microfluidic kidney mold variation of FIG. 15C, where an MM/SC spherical aggregate has been placed on either side of the UB cell chamber near the fluid connections and branching morphogenesis has begun.

Example 4: Immunostaining for Branching Morphogenesis

FIG. 16A-16B depict three images of the same embryonic kidney organoid generated using a microfluidic kidney mold device. FIG. 16A is a bright field image of a microfluidic kidney mold device as described in FIG. 15C that has been seeded with UB cells and two MM/SC spherical aggregates. The bright field image shows that branching morphogenesis between the UB cells and the MM/SC spherical aggregates has begun to form an embryonic kidney organoid. FIG. 16B shows the same embryonic kidney organoid that has been immunostained for UB cells. UB cells are present in the UB cell chamber, as expected, but have also branched into the MM/SC spherical aggregates. FIG. 16C shows the same embryonic kidney organoid that has been immunostained for MM/SC. MM/SC are present in the MM cell chambers, as expected, but have also branched into the UB cells.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of generating an embryonic kidney organoid, the method comprising the steps of:
    providing a kidney mold device having a ureteric bud (UB) cell chamber and a metanephric mesenchymal (MM) cell chamber, wherein the MM cell chamber is fluidly connected to the UB cell chamber;
    providing a precursor micromold having a plurality of channels for generating a UB tube from UB cells, wherein the channels are dimensioned such that UB tubes formed in the channels fit within the UB cell chamber of the kidney mold device;

seeding UB cells into the precursor micromold to generate a UB tube;

transferring the UB tube into the kidney mold device UB cell chamber;

generating a metanephric mesenchymal/stromal cell (MM/SC) aggregate or suspension;

transferring the MM/SC aggregate or suspension into the kidney mold device MM cell chamber; and culturing the kidney mold device in growth media to generate an embryonic kidney organoid.

2. The method of claim 1, wherein said UB cell chamber is linearly shaped.

3. The method of claim 1, wherein said MM cell chamber has the shape of an ellipse.

4. The method of claim 1, wherein said MM cell chamber has the shape of a bulb.

5. The method of claim 1, wherein said MM cell chamber has the shape of a circle.

6. The method of claim 1, wherein said kidney mold device is formed from a hydrogel.

7. The method of claim 1, wherein said kidney mold device is formed from a plastic polymer.

8. The method of claim 1, wherein said UB cell chamber and said MM cell chamber are incorporated into a microfluidic device.

9. The method of claim 1, wherein the kidney progenitor UB cells and MM/SC aggregate or suspension comprise embryonic cells differentiated towards the renal lineages of UB, MM, and stromal cells (SC).

10. The method of claim 1, wherein the kidney progenitor UB cells and MM/SC aggregate or suspension comprise induced pluripotent stem cells differentiated towards the renal lineages of UB, MM, and SC.

11. The method of claim 1, wherein the UB cells and MM/SC aggregate or suspension comprise urine derived stem cells differentiated towards the renal lineages of UB, MM, and SC.

12. The method of claim 1, wherein the cells and MM/SC aggregate or suspension comprise amniotic fluid stem cells differentiated towards the renal lineages of UB, MM, and SC.

13. The method of claim 1, further comprising the step of implanting said embryonic kidney organoid into a mammalian subject so that it can mature into a functional kidney.

14. The method of claim 13, wherein said embryonic kidney organoid is a human embryonic kidney organoid.

15. The method of claim 1, wherein the MM/SC are suspended in a medium selected from the group consisting of collagen, agarose, polyacrylamide, and matrigel.

16. The method of claim 1, wherein the MM/SC are aggregated into a sphere by overnight culture or by centrifugation.

17. The method of claim 1, wherein extracellular matrix (ECM) of an embryonic or adult kidney is added to the MM/SC aggregate or suspension.

18. A method of generating an embryonic kidney organoid, the method comprising the steps of:

providing a kidney mold device having a ureteric bud (UB) cell chamber and a metanephric mesenchymal (MM) cell chamber, wherein the MM cell chamber is fluidly connected to the UB cell chamber;

inserting a plug into the kidney mold device MM cell chamber;

seeding UB cells into the kidney mold device UB cell chamber to generate a UB tube;

removing the plug by extraction or dissolution;

generating a MM/somatic cell aggregate or suspension;

transferring the MM/somatic cell aggregate or suspension into the kidney mold device MM cell chamber; and culturing the kidney mold device in growth media to generate an embryonic kidney organoid.

19. The method of claim 18, wherein the plug comprises a dissolvable material selected from the group consisting of gelatin, hydrogel, and polymer.

* * * * *